United States Patent
Murakami et al.

(10) Patent No.: US 6,909,023 B2
(45) Date of Patent: Jun. 21, 2005

(54) PRODUCTION METHOD FOR BENZENEDIMETHANOL COMPOUND

(75) Inventors: Masatoshi Murakami, Kawasaki (JP); Yuseki Suyama, Kawasaki (JP); Kohei Morikawa, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 222 days.

(21) Appl. No.: 10/311,801

(22) PCT Filed: Jul. 3, 2001

(86) PCT No.: PCT/JP01/05759

§ 371 (c)(1),
(2), (4) Date: Dec. 20, 2002

(87) PCT Pub. No.: WO02/02504

PCT Pub. Date: Jan. 10, 2002

(65) Prior Publication Data

US 2003/0171626 A1 Sep. 11, 2003

Related U.S. Application Data

(60) Provisional application No. 60/221,922, filed on Jul. 31, 2000.

(30) Foreign Application Priority Data

Jul. 4, 2000 (JP) ........................................ 2000-202786

(51) Int. Cl.[7] .............................................. C07C 25/13
(52) U.S. Cl. ...................... 570/143; 558/411; 558/425; 570/123
(58) Field of Search ................................. 558/411, 425; 570/123, 143

(56) References Cited

U.S. PATENT DOCUMENTS

| | | | | |
|---|---|---|---|---|
| 4,140,843 A | * | 2/1979 | Widmer et al. ............. | 570/129 |
| 4,178,293 A | | 12/1979 | Henrick et al. | |
| 4,189,589 A | | 2/1980 | Meyer et al. | |
| 4,217,303 A | * | 8/1980 | Drake ......................... | 558/377 |
| 5,869,653 A | | 2/1999 | Johnson | |
| 6,018,048 A | * | 1/2000 | Morikawa et al. .......... | 546/185 |
| 6,339,176 B2 | * | 1/2002 | Hirose et al. ............... | 568/628 |
| 6,759,558 B2 | * | 7/2004 | Rodefeld .................... | 568/811 |

FOREIGN PATENT DOCUMENTS

| | | |
|---|---|---|
| EP | 0 099 622 | 2/1984 |
| EP | 1 114 809 | 7/2001 |
| GB | 2-127-013 A | 4/1984 |
| GB | 2 127 013 | 4/1984 |
| JP | 59 157039 | 9/1984 |
| JP | 60-35331 B2 | 8/1985 |
| JP | 61-1056 B2 | 1/1986 |
| JP | 1-238555 A | 9/1989 |
| JP | 4-14096 A | 1/1992 |
| JP | 2000-86583 A | 3/2000 |
| JP | 2000-086583 | 3/2000 |

OTHER PUBLICATIONS

M. Tashiro, et al. "Metacyclophanes and Related Compounds." *Journal of Organic Chemistry*. vol. 54, 1989, pp. 2012–2015.

* cited by examiner

*Primary Examiner*—Golam M M Shameem
(74) *Attorney, Agent, or Firm*—Sughrue Mion, PLLC

(57) ABSTRACT

To provide a novel method for producing a fluorinated benzenedimethanol compound useful as a starting material or an intermediate in the production of agricultural or medicinal chemicals in an industrially advantageous manner.

A method for producing a fluorinated benzenedimethanol compound according to the present invention comprises the steps of reducing the nitrile groups of a fluorinated benzenedinitrile compound to obtain a fluorinated xylylenediamine compound and then converting the aminomethyl groups of the fluorinated xylylenediamine compound into hydroxymethyl groups.

10 Claims, No Drawings

PRODUCTION METHOD FOR BENZENEDIMETHANOL COMPOUND

CROSS REFERENCE OF RELATED APPLICATION

This application is a Natural Stage of PCT/JP01/05759 filed Jul. 3, 2001, which claims benefit pursuant to 35 U.S.C. §119(e) of the filing date of Provisional Application No. 60/221,922 filed on Jul. 31, 2000, pursuant to 35 U.S.C. §111(b).

DETAILED DESCRIPTION OF THE INVENTION

1. Technical Field

The present invention relates to a novel method for producing fluorinated benzenedimethanol compounds useful as a starting material or an intermediate in the production of agricultural or medicinal chemicals. In particular, tetrafluorobenzenedimethanol is useful as an intermediate in the production of cyclopropanecarboxylic acid esters having excellent insecticidal activity.

2. Background Art

Cyclopropanecarboxylic acid esters of tetrafluorobenzenedimethanol are known to have high insecticidal activity (see, JP-A-1-238555 (the term "JP-A" as used herein means an "unexamined published Japanese patent application")).

With respect to the method for producing tetrafluorobenzenedimethanol, for example, British Unexamined Patent Publication No. 2,127,013 discloses a method of reducing 2,3,5,6-tetrafluoroterephthalic acid chloride by NaBH$_4$, U.S. Pat. Nos. 4,189,589 and 4,178,293 disclose a method of reducing 2,3,4,5-tetrafluorophthalic acid with diborane, and JP-A-1-238555 discloses a method where 2,3,5,6-tetrafluorotoluene and methyl iodide are reacted in the presence of n-butyllithium to obtain 2,3,5,6-tetrafluoroxylene and thereafter, the methyl group is brominated, acetylated and then hydrolyzed to produce 2,3,5,6-tetrafluorobenzenedimethanol.

These methods are, however, not advantageous in industry because an expensive reducing agent is used or the process takes a long time.

The reaction of reducing the later-described fluorinated benzenedinitrile compound represented by formula (1) to produce the later-described fluorinated xylylenediamine compound represented by formula (2) is known. For example, JP-A-4-14096 discloses a method of hydrogenating 2,3,5,6-tetrafluoroterephthalonitrile in the presence of a hydrogenation catalyst to produce a corresponding tetrafluoroxylylenediamine.

The method of reacting xylylenediamine and a nitrite in an acidic aqueous solution to produce benzenedimethanol is also known. For example, JP-B-61-1056 (the term "JP-B" as used herein means an "examined Japanese patent publication") discloses a method of reacting xylylenediamine and a nitrite in the presence of water and a mineral acid to produce benzenedimethanol.

Furthermore, JP-B-60-35331 discloses a method of reacting xylylenediamine and a nitrite in the presence of a carboxylic acid and water to obtain a mixture of benzenedimethanol and mono- and di-carboxylic acid esters of benzenedimethanol and then hydrolyzing it to produce benzenedimethanol.

In addition, JP-A-2000-86583 discloses a method of subjecting a fluorine-containing benzonitrile derivative to a reduction reaction to thereby obtain a fluorine-containing benzylamine derivative and then displacing the amino group of the fluorine-containing benzylamine derivative by a hydroxyl group to produce a fluorine-containing benzylalcohol derivative.

Heretofore, however, no report has been made on the case where a fluorinated benzenedimethanol compound useful as a starting material, an intermediate or a monomer in the production of agricultural and medicinal chemicals is produced from fluorinated benzenedinitrile through a fluorinated xylylenediamine compound.

In the case of displacing the amino group by a hydroxyl group using a nitrite in the presence of an acid, a method of keeping a mixture of an amino group-containing compound and an acid at a predetermined temperature and adding thereto a nitrite or an aqueous solution thereof is generally employed. JP-B-61-1056, JP-B-60-35331 and JP-A-2000-86583 supra also clearly state that the method of adding a nitrite while keeping an amine and an acid at a predetermined temperature is a preferred reaction form. However, according to the studies by the present inventors, it has been found that when this method generally recognized as a preferred reaction form is employed for a fluorinated xylylenediamine compound represented by formula (2), namely, a nitrite is added while keeping the fluorinated xylylenediamine compound and an acid at a predetermined temperature, the product precipitates and due to nitrogen generated with the progress of the reaction, bubbling occurs. Thus, this method is not a fully satisfactory reaction form in the industrial use. A more improved production method is being demanded, however, such an improved method is not known or clearly described at the present time. Under these circumstances, the above-described problem remains unsolved.

Problems to be Solved by the Invention

The object of the present invention is to provide a method for producing a fluorinated benzenedimethanol compound useful as a starting material or an intermediate in the production of agricultural or medicinal chemicals, which can be implemented in an industrially advantageous manner. An improved modification of the production method is also provided.

Means to Solve the Problems

The present invention comprises the following matters.

[1] A method for producing a fluorinated benzenedimethanol compound, comprising reducing the nitrile groups of a fluorinated benzenedinitrile compound represented by formula (1):

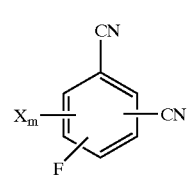

(1)

(wherein X represents a chlorine atom or a fluorine atom, and m represents an integer of from 0 to 3, provided that when m is 2 or more, X may be the same or different) to obtain a fluorinated xylylenediamine compound represented by formula (2):

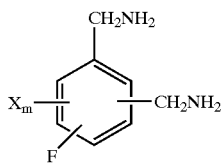

(2)

(wherein X and m have the same meanings as defined above), and converting the aminomethyl groups of the fluorinated xylylenediamine compound into hydroxymethyl groups to produce a fluorinated benzenedimethanol compound represented by formula (3):

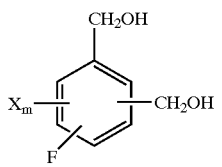

(3)

(wherein X and m have the same meanings as defined above).

[2] The method for producing a fluorinated benzenedimethanol compound as described in [1], wherein the conversion of the aminomethyl groups of a fluorinated xylylenediamine compound represented by formula (2) into hydroxymethyl groups is performed by preparing a mixture containing a fluorinated xylylenediamine compound represented by formula (2) and a nitrite, and then adding thereto and reacting therewith an acid.

[3] The method for producing a fluorinated benzenedimethanol compound as described in [2], wherein the acid is a carboxylic acid represented by the following formula (4):

R—COOH (4)

(wherein R represents an alkyl having 1 to 8 carbon atoms or aryl group having from 6 to 8 carbon atoms).

[4] The method for producing a fluorinated benzenedimethanol compound as described in [3], wherein the carboxylic acid is acetic acid.

[5] The method for producing a fluorinated benzenedimethanol compound as described in [3] or [4], wherein after the addition of an acid, hydrolysis is performed.

[6] The method for producing a fluorinated benzenedimethanol compound as described in [5], wherein the hydrolysis reaction is performed using a carbonate or hydrogen carbonate of an alkali metal.

[7] The method for producing a fluorinated benzenedimethanol compound as described in any one of [1] to [6], wherein in reducing the nitrile groups of a fluorinated benzenedinitrile compound represented by formula (1) to obtain a fluorinated xylylenediamine compound represented by formula (2), the reduction is performed with hydrogen in the presence of a metal catalyst.

[8] The method for producing a fluorinated benzenedimethanol compound as described in [7], wherein the metal catalyst is sponge nickel.

[9] The method for producing a fluorinated benzenedimethanol compound as described in [8], wherein the sponge nickel is heated with stirring in a solvent under hydrogen pressure before it is used in the reaction.

[10] The method for producing a fluorinated benzenedimethanol compound as described in any one of [7] to [9], wherein the amount of the metal catalyst used is from 0.01 to 1 times by mass based on the fluorinated benzenedinitrile compound.

[11] The method for producing a fluorinated benzenedimethanol compound as described in any one of [1] to [10], wherein the fluorinated benzenedinitrile compound represented by formula (1) is tetrafluoroterephthalonitrile or tetrafluoroisophthalonitrile and the corresponding fluorinated benzenedimethanol compound represented by formula (3) is 2,3,5,6-tetrafluorobenzenedimethanol or 2,4,5,6-tetrafluorobenzenedimethanol.

MODE FOR CARRYING OUT THE INVENTION

The present invention is described in detail below.

The fluorinated benzenedinitrile compound represented by formula (1) used as a starting material in the present invention is commercially available and can be easily purchased. The positions to which two nitrile groups are bonded in formula (1) are not limited.

Specific examples of the fluorinated benzenedinitrile compound represented by formula (1) include tetrafluoroisophthalonitrile, tetrafluoroterephthalonitrile, tetrafluorophthalonitrile and 2,4,6-trifluoro-5-chloro-isophthalonitrile.

For reducing the fluorinated benzenedinitrile compound represented by formula (1) of the present invention into a fluorinated xylylenediamine compound represented by formula (2) (hereinafter sometimes also referred to as a "reduction reaction"), a conventionally known reduction method may be used. Particularly, a method of reducing the compound with hydrogen in the presence of hydrogenation catalyst is preferred. Examples of the hydrogenation catalyst include metal catalysts such as nickel, palladium, platinum, ruthenium, cobalt and copper. The catalyst may be a metal itself or may be a supported catalyst. The support which can be used is activated carbon, silica, alumina or the like. Specific preferred examples of the catalyst include sponge nickel, sponge cobalt and palladium/activated carbon.

In the case of using sponge nickel or sponge cobalt as the catalyst, the catalyst is preferably subjected to a pretreatment before the reduction reaction so as to improve the activity and selectivity. The pretreatment of the catalyst is performed by heating the catalyst with stirring under hydrogen pressure in a solvent of 1 to 20 times by mass based on the catalyst. The hydrogen pressure is not particularly limited and may be from atmospheric pressure to applied pressure, however, the reaction is preferably performed under a hydrogen partial pressure from atmospheric pressure to 1 MPa. The reaction temperature is preferably from 30 to 150° C., more preferably from 60 to 150° C. Examples of the solvent for use in the pretreatment of the catalyst include alcohols such as methanol, ethanol and 2-propanol, ethers such as 1,4-dioxane, 1,3-dioxolan and tetrahydrofuran, aromatic hydrocarbons such as benzene, xylene, toluene and mesitylene, and aliphatic hydrocarbons such as hexane or cyclohexane, and these may be used individually or as a mixed solvent of two or more thereof. Among those, preferred are methanol, 1,4-dioxane and 1,3-dioxolan.

The amount of the hydrogenation catalyst used is preferably from 0.01 to 1 times by mass, more preferably from 0.1 to 0.5 times by mass, based on the fluorinated benzenedinitrile compound represented by formula (1).

Examples of the solvent used for the reduction reaction of the present invention include alcohols such as methanol, ethanol and 2-propanol, ethers such as 1,4-dioxane, 1,3-dioxolan and tetrahydrofuran, aromatic hydrocabons such as benzene, xylene, toluene and mesitylene, aliphatic hydrocarbons such as hexane and cyclohexane, and these may be used individually or as a mixed solvent of two or more thereof. Among those, preferred are methanol, 1,4-dioxane, 1,3-dioxolan and toluene. The amount of the solvent is preferably from 1 to 100 times by mass, more preferably from 2 to 20 times by mass, based on the fluorinated benzencnitrile compound represented by formula (1).

The reaction form is not particularly limited but a catalyst suspension flow system, a fixed bed flow system, a trickle bed system or a batch system may be used.

The reaction temperature is not particularly limited, however, the reaction is preferably performed at a temperature from an ordinary temperature to around 150° C. The reaction pressure may be from atmospheric pressure to applied pressure, however, the reaction is preferably performed under a pressure from atmospheric pressure to 2 MPa, more preferably from atmospheric pressure to 1 MPa.

The fluorinated xylylenediamine compound represented by formula (2) produced according to the reduction reaction of the present invention may be isolated and purified by separating the catalyst from the reaction solution after the reduction reaction through an operation such as filtration, centrifugation or precipitation, and then distilling or extracting the residue, or the compound may be used in the next process without isolating it.

Specific examples of the fluorinated xylylenediamine compound represented by formula (2) include 2,4,5,6-tetrafluoroxylylenediamine, 2,3,5,6-tetrafluoroxylylenediamine, 2,3,4,5-tetrafluoroxylylenediamine and 2,4,6-trifluoro-5-chloroxylylenediamine.

The reaction of converting the aminomethyl groups of the fluorinated xylylenediamine compound represented by formula (2) of the present invention into hydroxymethyl groups to obtain a fluorinated benzenedimethanol compound represented by formula (3) is performed by reacting the fluorinated xylylenediamine compound with a nitrite in the presence of an acid (hereinafter sometimes also referred to as "diazotization reaction"). Due to the nitrous acid generated from a nitrite and an acid, the amino group is converted into a diazonium compound. This reaction is called a diazotization reaction. The thus-obtained diazonium compound is considered to decompose due to water while generating nitrogen and thereby produce a hydroxyl group.

The diazotization reaction for use in the present invention may be performed using a general reaction form such that a mixture of an amino group-containing compound and an acid is kept at a predetermined temperature and thereto, a nitrite or an aqueous nitrite solution is added. In this case, however, the product precipitates and due to nitrogen generated with the progress of the reaction, the reaction solution may undergo abrupt elevation of the liquid surface or the like, therefore, the practice in industry requires great care. The diazotization reaction is preferably performed by a method where the addition order is reversed to the above-described conventional method, that is, a mixture of a fluorinated xylylenediamine compound represented by formula (2) and a nitrite is prepared and then an acid is added thereto. In the case of using this method, the fluorinated benzenedimethanol compound produced does not precipitate in the reaction solution and the reaction solution can be prevented from occurrence of bubbling.

The problems such as bubbling encountered in using the above-described general reaction form for the diazotization reaction of the present invention seem to be ascribable to the properties peculiar to the product fluorinated benzenedimethanol compound, more specifically, high melting point because of dimethanol and low solubility in the reaction solution since the product is fluorinated. For example, the melting point of a fluorinated benzyl alcohol is from 43 to 44° C. in the case of 2,3,6-trifluorobenzylalcohol and 32° C. in the case of pentafluorobenzyl alcohol. On the other hand, the melting point of 2,3,5,6-tetrafluorobenzendimethanol is 120° C. or more. Thus, the melting point of fluorinated benzenedimethanol is greatly elevated as compared with the melting point of fluorinated benzyl alcohol. Furthermore, the solubility of 1,4-benzenedimethanol in water at room temperature is about 57 g/L, whereas the solubility of 2,3,5,6-tetrafluorobenzenedimethanol in water at room temperature is about 25 g/L. Thus, the solubility of fluorinated benzenedimethanol is greatly reduced as compared with the solubility of benzenedimethanol. In addition, in the case of using a carboxylic acid as the acid for the diazotization reaction of the present invention, the fact that the mono- and di-carboxylic acid esters produced are extremely low in the solubility in water is considered also responsible for the problems.

The nitrite used for the diazotization reaction of the present invention is preferably sodium nitrite or potassium nitrite. The amount of the nitrite used is preferably from 2 to 5 times in mol, more preferably from 2 to 3 times in mol, based on the fluorinated xylylenediamine compound represented by formula (2).

The acid used for the reaction is a mineral acid or a carboxylic acid represented by formula (4). Examples of the mineral acid include sulfuric acid, nitric acid and phosphoric acid, and examples of the carboxylic acid include formic acid, acetic acid and propionic acid.

The amount of the mineral acid or carboxylic acid used is preferably from 2 to 5 times in mol, more preferably from 2 to 2.5 times in mol, based on the fluorinated xylylenediamine compound represented by formula (2).

In order to decompose the produced diazonium compound into a hydroxyl group subsequently to the diazotization reaction of the present invention, water is needed and the water produced at the diazotization reaction can undertake the part. In the case of using the diazotization reaction form of preparing a mixture of the fluorinated xylylenediamine compound represented by formula (2) and a nitrite and then adding an acid thereto, water is preferably added before adding the acid to the mixture of the fluorinated xylylenediamine compound represented by formula (2) and a nitrite, because thorough stirring can be attained. In this case, the amount of water added is preferably from 1 to 20 times by mass, more preferably from 2.5 to 10 times by mass, based on the fluorinated xylylenediamine compound represented by formula (2).

The reaction temperature is not particularly limited but is preferably from 0 to 100° C., more preferably from 0 to 50° C. It is preferred to set the fluorinated xylylenediamine compound represented by formula (2), nitrite and water to a reaction temperature in the above-described range and while maintaining the temperature, add an acid. The acid may be added as it is or in the form of an aqueous solution. In the case of using a mineral acid as the acid, a fluorinated benzenedimethanol compound represented by formula (3) is obtained and in the case of using a carboxylic acid represented by formula (4) as the acid, mono- and di-carboxylic acid esters of the fluorinated benzenedimethanol compound represented by formula (3) remain together with the objective fluorinated benzenedimethanol represented by formula (3). From these mono- and di-carboxylic acid esters, the fluorinated benzenedimethanol compound represented by formula (3) can be obtained by hydrolyzing the mono- and di-carboxylic acid esters. After the completion of dropwise addition of the acid, when the solution is stirred at the same temperature or under heating, hydrolysis proceeds. The hydrolysis reaction may also be performed by adding an alkali. The alkali added is not particularly limited but a weak alkali such as sodium hydrogen carbonate or potassium hydrogen carbonate is preferred.

After the completion of the reaction of the present invention, the resulting fluorinated benzenedimethanol compound represented by formula (3) may be isolated and purified by extraction, solvent distillation or recrystallization.

Specific examples of the fluorinated benzenedimethanol compound represented by formula (3) include compounds such as 2,4,5,6-tetrafluorobenzenedimethanol, 2,3,5,6-tetrafluorobenzenedimethanol, 2,3,4,5-tetrafluorobenzenedimethanol and 2,4,6-trifluoro-5-chlorobenzenedimethanol.

Effects of the Invention

According to the production method of the present invention, a fluorinated benzenedimethanol compound useful as an intermediate or the like in the production of agricultural or medicinal chemicals can be produced in an industrially advantageous manner.

EXAMPLES

The present invention is described below by referring to the Examples, however, the present invention is by no means limited to these Examples.

Example 1

Synthesis of 2,3,5,6-tetrafluoroxylylenediamine

Into a 500 ml-volume stainless steel-made autoclave, 5.0 g of sponge nickel catalyst R210 (produced by NIKKO RIKA) and 50 g of methanol were charged, then the hydrogen pressure therein was set to 0.2 MPa at room temperature. Heating and stirring of the autoclave were started and when the temperature reached 110° C., the autoclave was kept at said temperature for 1 hour and then cooled. Into this autoclave, 20.0 g (100 mmol) of 2,3,5,6-tetrafluoroterephthalonitrile and 125 g of methanol were charged and then the hydrogen pressure therein was set to 0.85 MPa at room temperature. While keeping the pressure at 0.85 MPa, heating and stirring of the autoclave were started. One hour after the temperature reached 80° C., hydrogen absorption stopped. Then, the reaction solution was cooled, the catalyst was removed by filtration, the solvent was removed by distillation and the residue was distilled under reduced pressure, as a result, 18.3 g of 2,3,5,6-tetrafluoroxylylenediamine was obtained as white crystals. The purity determined from the GC area in percentage was 99.2% and the yield was 87.2%.

Example 2

Synthesis of 2,3,5,6-tetrafluorobenzenedimethanol

Into a 200 ml-volume flask equipped with a thermometer, a stirring unit, a nitrogen inlet and a reflux condenser, 10.4 g (50.0 mmol) of 2,3,5,6-tetrafluoroxylylenediamine synthesized in Example 1, 50 g of water and 10.35 g (150.0 mmol) of sodium nitrite were charged, and the mixture was stirred at room temperature for 30 minutes. Subsequently, under cooling of the reactor in a water bath, 7.51 g (125.0 mmol) of acetic acid was added dropwise over 60 minutes while keeping the inside of the reaction system at 40° C. or less. After the completion of dropwise addition of acetic acid, 0.8 g of sodium hydrogencarbonate was charged, and the mixture solution was further stirred at 40° C. for 60 minutes. The reaction solution obtained was extracted with 10.0 g of methyl ethyl ketone, the organic phase was washed with 5.0 g of an aqueous 5 mass % sulfuric acid solution, and then the methyl ethyl ketone was removed by distillation, as a result, 9.1 g of 2,3,5,6-tetrafluorobenzenedimethanol was obtained as white crystals. The purity determined from the GC area in percentage was 98.9% and the yield was 85.7%.

Example 3

Synthesis of 2,3,5,6-tetrafluorobenzenedimethanol

Into a 200 ml-volume flask equipped with a thermometer, a stirring unit, a nitrogen inlet and a reflux condenser, 10.4 g (50.0 mmol) of 2,3,5,6-tetrafluoroxylylenediamine synthesized in Example 1, 50 g of water and 10.35 g (150.0 mmol) of sodium nitrite were charged, and the mixture was stirred at room temperature for 30 minutes. Subsequently, under cooling of the reactor in a water bath, 6.13 g (62.5 mmol) of sulfuric acid was added dropwise over 60 minutes while keeping the inside of the reaction system at 40° C. or less. The reaction solution obtained was extracted with 10.0 g of methyl ethyl ketone, the organic phase was washed with 5.0 g of an aqueous 5 mass % sulfuric acid solution, and then the methyl ethyl ketone was removed by distillation, as a result, 7.9 g of 2,3,5,6-tetrafluorobenzenedimethanol was obtained as white crystals. The purity determined from the GC area in percentage was 98.3% and the yield was 73.9%.

Example 4

Synthesis of 2,3,5,6-tetrafluoroxylylenediamine

Into a 500 ml-volume stainless steel-made autoclave, 5.0 g of sponge nickel catalyst R210 (produced by NIKKO RIKA), 20.0 g of tetrafluoroterephthalonitrile and 175 g of methanol were charged, and then the hydrogen pressure therein was set to 0.85 MPa at room temperature. While keeping the pressure at 0.85 MPa, heating and stirring of the autoclave was started. 50 Minutes after the temperature reached 80° C., the hydrogen absorption stopped. Then, the reaction solution was cooled, the catalyst was removed by filtration, the solvent was removed by distillation and the residue was distilled under reduced pressure, as a result, 10.3 g of white crystals were obtained. The white crystal obtained was analyzed by GC and found to be a mixture of 2,3,5,6-tetrafluoroxylylenediamine and 2,3,5,6-tetrafluoro-4-cyanobenzylamine. The GC area ratio of 2,3,5,6-tetrafluoroxylylenediamine to 2,3,5,6-tetrafluoro-4-cyanobenzylamine was 23/77.

Example 5

Synthesis of 2,3,5,6-tetrafluorobenzenedimethanol

Into a 200 ml-volume flask equipped with a thermometer, a stirring unit, a nitrogen inlet and a reflux condenser, 10.4 g (50.0 mmol) of 2,3,5,6-tetrafluoroxylylenediamine synthesized in Example 1, 50 g of water and 9.0 g (150.0 mmol) of acetic acid were charged, and the mixture was stirred at room temperature for 30 minutes. Subsequently, under cooling of the reactor in a water bath, 21.56 g (125.0 mmol) of an aqueous 40 mass % sodium nitrite solution was added dropwise while keeping the inside of the reaction system at 40° C. or less. At the time when about 30% of an aqueous sodium nitrite solution was charged into the reaction system, insoluble components precipitated in the system and vigorous bubbling occurred. Therefore, the dropwise addition of an aqueous sodium nitrite solution was stopped until the bubbling calmed. After the disappearance of bubbling, the dropwise addition of an aqueous sodium nitrite solution was re-started but bubbling was again generated. The operation of re-starting the dropwise addition of sodium nitrite after the disappearance of bubbling was repeated and after 5 hours and 20 minutes, the dropwise addition was completed. The reaction solution obtained was extracted with 10.0 g of methyl ethyl ketone, the organic phase was washed with 5.0 g of an aqueous 5 mass % sulfuric acid solution, and then the methyl ethyl ketone was removed by distillation, as a result, 8.9 g of 2,3,5,6-tetrafluorobenzenedimethanol was obtained as white crystals. The purity determined from the GC area in percentage was 97.9% and the yield was 82.9%.

What is claimed is:

1. A method for producing a fluorinated benzenedimethanol compound, comprising reducing the nitrile groups of a fluorinated benzenedinitrile compound represented by formula (1):

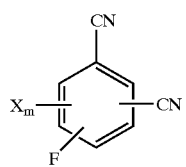

(1)

(wherein X represents a chlorine atom or a fluorine atom, and m represents an integer of from 0 to 3, provided that when m is 2 or more, X may be the same or different) to obtain a fluorinated xylylenediamine compound represented by formula (2):

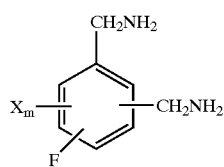

(2)

(wherein X and m have the same meanings as defined above), and converting the aminomethyl groups of said fluorinated xylylenediamine compound into hydroxymethyl groups by preparing a mixture containing the fluorinated xylylenediamine compound represented by formula (2) and a nitrite, and then adding an acid to the mixture to produce a fluorinated benzenedimethanol compound represented by formula (3):

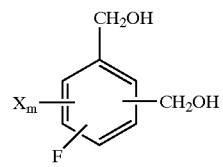

(3)

(wherein X and m have the same meanings as defined above).

2. The method for producing a fluorinated benzenedimethanol compound as claimed in claim 1, wherein the acid is a carboxylic acid represented by the following formula (4):

R—COOH    (4)

(wherein R represents an alkyl having 1 to 8 carbon atoms or aryl group having from 6 to 8 carbon atoms).

3. The method for producing a fluorinated benzenedimethanol compound as claimed in claim 2, wherein the carboxylic acid is acetic acid.

4. The method for producing a fluorinated benzenedimethanol compound as claimed in claim 2 or 3, wherein after the addition of an acid, hydrolysis is performed.

5. The method for producing a fluorinated benzenedimethanol compound as claimed in claim 4, wherein the hydrolysis reaction is performed using a carbonate or hydrogen carbonate of an alkali metal.

6. The method for producing a fluorinated benzenedimethanol compound as claimed claim 1, wherein in reducing the nitrile groups of a fluorinated benzenedinitrile compound represented by formula (1) to obtain a fluorinated xylylenediamine compound represented by formula (2), the reduction is performed with hydrogen in the presence of a metal catalyst.

7. The method for producing a fluorinated benzenedimethanol compound as claimed in claim 6, wherein the metal catalyst is sponge nickel.

8. The method for producing a fluorinated benzenedimethanol compound as claimed in claim 7, wherein the sponge nickel is heated with stirring in a solvent under hydrogen pressure before it is used in the reaction.

9. The method for producing a fluorinated benzenedimethanol compound as claimed in claim 6, wherein the amount of the metal catalyst used is from 0.01 to 1 times by mass based on the fluorinated benzenedinitrile compound.

10. The method for producing a fluorinated benzenedimethanol compound as claimed in claim 1, wherein the fluorinated benzenedinitrile compound represented by formula (1) is tetrafluoroterephthalonitrile or tetrafluoroisophthalonitrile and the corresponding fluorinated benzenedimethanol compound represented by formula (3) is 2,3,5,6-tetrafluorobenzenedimethanol or 2,4,5,6-tetrafluorobenzenedimethanol.

* * * * *